(12) United States Patent
Kerselaers et al.

(10) Patent No.: US 10,389,406 B2
(45) Date of Patent: Aug. 20, 2019

(54) NEAR-FIELD DEVICE

(71) Applicant: NXP B.V., Eindhoven (NL)

(72) Inventors: Anthony Kerselaers, Herselt (BE);
Pieter Verschueren, Langdorp (BE);
Liesbeth Gommé, Anderlecht (BE)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 15/642,168

(22) Filed: Jul. 5, 2017

(65) Prior Publication Data
US 2019/0013839 A1 Jan. 10, 2019

(51) Int. Cl.
*H04B 5/00* (2006.01)
*G01N 27/72* (2006.01)

(52) U.S. Cl.
CPC ......... *H04B 5/0012* (2013.01); *H04B 5/0043* (2013.01); *H04B 5/0081* (2013.01); *G01N 27/72* (2013.01)

(58) Field of Classification Search
CPC .... H04B 5/0081; H04B 85/05; H04B 5/0012; G01N 2035/00346; G01N 2333/75; G01N 22/00; G01N 33/536; Y10S 436/805; Y10S 436/806; A61B 5/14546; A61B 5/05; A61B 5/0507; A61B 5/14532
See application file for complete search history.

(56) References Cited

U.S. PATENT DOCUMENTS

| | | | |
|---|---|---|---|
| 2,438,795 A | 3/1948 | Wheeler | |
| 2,685,068 A | 7/1954 | Goubau | |
| 4,639,669 A | 1/1987 | Howard et al. | |
| 4,743,916 A | 5/1988 | Bengeult | |
| 5,341,100 A | 8/1994 | Taylor | |
| 5,341,102 A | 8/1994 | Akiyama et al. | |
| 5,973,503 A | 10/1999 | Kuipers et al. | |
| 6,426,629 B1 | 7/2002 | Edgson et al. | |
| 6,691,563 B1 | 2/2004 | Trabelsi et al. | |
| 7,009,471 B2 | 3/2006 | Elmore | |
| 7,567,154 B2 | 7/2009 | Elmore | |
| 8,664,965 B2 | 3/2014 | Calciolari et al. | |
| 8,724,835 B2 | 5/2014 | Kerselaers et al. | |
| 9,042,812 B1 | 5/2015 | Bennett et al. | |
| 9,197,986 B1 | 11/2015 | Kerselaers et al. | |
| 2002/0155625 A1* | 10/2002 | Chapman | G01N 22/00 436/536 |
| 2006/0063488 A1 | 3/2006 | Hraby et al. | |

(Continued)

OTHER PUBLICATIONS

RF cavities, Nassiri, 2010 http://uspas.fnal.gov/materials/10MIT/Lecture12.pdf (Year: 2010).*

(Continued)

*Primary Examiner* — Jianxun Yang (57) ABSTRACT

One example discloses a near-field device, comprising: a near-field receiver coupled to a near-field receiver antenna and a decoder circuit; wherein the near-field receiver antenna is configured to be capacitively coupled at a first location of a first substance; wherein the near-field receiver antenna is configured to receive a first near-field signal from the first substance through the receiver's capacitive coupling; and wherein the decoder circuit is configured to compare an attribute of the first near-field signal to an attribute of a second near-field signal received from a second substance.

20 Claims, 6 Drawing Sheets

(56) References Cited

U.S. PATENT DOCUMENTS

| | | | |
|---|---|---|---|
| 2006/0235633 A1* | 10/2006 | Simons | G01R 29/0892 702/65 |
| 2008/0306359 A1 | 12/2008 | Zdeblick et al. | |
| 2008/0319285 A1* | 12/2008 | Hancock | A61B 5/05 600/309 |
| 2016/0047768 A1 | 2/2016 | Dabelstein et al. | |
| 2016/0110639 A1 | 4/2016 | Finn et al. | |

OTHER PUBLICATIONS

Wikipedia; "Magnetic particle inspection"; retrieved from the internet on May 22, 2017 https://en.wikipedia.org/wiki/Magnetic_particle_inspection; 6 pages May 22, 2017.

U.S. Appl. No. 15/602,160, filed May 23, 2017; not yet published.

Restriction/Election, U.S. Appl. No. 15/602,160; 6 pages (dated May 4, 2018).

Non Final Office Action, U.S. Appl. No. 15/602,160; 35 pages (dated Jul. 24, 2018.

Diamond, G. et al., "A New Capacitive Imaging Technique for NDT", 9th European Conference on NDT, ECNDT, Nov. 1, 2006, pp. 1-8, retrieved from the Internet at http://www.ndt.net/article/ecndt2006/doc/P229.pdf on Nov. 1, 2006.

Liu, Zheng et al., "Experimenting Capacitive Sensing Technique for Structural Integrity Assessment", 2017 IEEE International Conference on Industrial Technology (ICIT), Mar. 22, 2017, pp. 922-927, IEEE, Piscataway, NJ, USA.

Final Office Action, U.S. Appl. No. 15/602,160; 20 pages (dated Oct. 9, 2018).

Nassiri, A.: "RF Cavities"; http://uspas.final.gov/materials/10MIT/Lecture12.pdf; 61 page (2010).

* cited by examiner

NEAR-FIELD DEVICE

The present specification relates to systems, methods, apparatuses, devices, articles of manufacture and instructions for near-field signal analysis.

SUMMARY

According to an example embodiment, a near-field device, comprising: a near-field receiver coupled to a near-field receiver antenna and a decoder circuit; wherein the near-field receiver antenna is configured to be capacitively coupled at a first location of a first substance; wherein the near-field receiver antenna is configured to receive a first near-field signal from the first substance through the receiver's capacitive coupling; and wherein the decoder circuit is configured to compare an attribute of the first near-field signal to an attribute of a second near-field signal received from a second substance.

In another example embodiment, the decoder circuit is configured to indicate the first substance is same as the second substance if the attribute of the first substance is within a predetermined range of the attribute of the second substance.

In another example embodiment, the decoder circuit is configured to indicate the first substance is different from the second substance if the attribute of the first substance is outside of a predetermined range of the attribute of the second substance.

In another example embodiment, the decoder circuit is configured to assign a quality level to the first substance based on how close the attribute of the first substance is to the attribute of the second substance.

In another example embodiment, the first substance includes at least one of: liquid, solid, gas, plasma, saline, glucose, insulin, a structure, an assembly of parts, a mixture, a food, or a set of items.

In another example embodiment, the attribute of the received near-field signal is at least one of: a signal strength, a signal to noise ratio, a voltage, an attenuation, a conductivity, or another electrical parameter.

In another example embodiment, the attribute of the first near-field signal is affected by at least one of the first substance characteristics: an atomic characteristic, a molecular characteristic, a cellular characteristic, a mixture characteristic, a structural characteristic, a conductive characteristic, a quantity characteristic, or a volume characteristic.

In another example embodiment, the capacitive coupling between the receiver antenna and the first substance includes at least one of: an air gap or a container.

In another example embodiment, further comprising a container configured to hold the first substance.

In another example embodiment, the first substance is more conductive than the container.

In another example embodiment, the near-field receiver antenna substantially conforms to a shape of the container.

In another example embodiment, the near-field receiver antenna is configured to physically hold the container.

In another example embodiment, the first near-field signal includes a carrier frequency that is ≤30 MHz.

In another example embodiment, further comprising: another near-field device including a near-field transmitter coupled to a near-field transmitter antenna and an encoder circuit; wherein the near-field transmitter antenna is configured to be capacitively coupled at a second location on the first substance; wherein the encoder circuit is configured to generate the first near-field signal; and wherein the near-field transmitter antenna is configured to transmit the first near-field signal to the first substance through the transmitter's capacitive coupling.

In another example embodiment, the receiver and transmitter antennas are configured to physically hold the first substance.

In another example embodiment, the receiver and transmitter antennas are configured to permit the first substance to be removed and replaced with additional substances.

In another example embodiment, the first near-field signal is generated by an electric near-field antenna in the transmitter antenna and received by a magnetic near-field antenna in the receiver antenna.

In another example embodiment, the first near-field signal is generated by a magnetic near-field antenna in the transmitter antenna and received by an electric near-field antenna in the receiver antenna.

According to an example embodiment, a method of processing a near-field signal, comprising: receiving a first near-field signal from a first substance through a capacitive coupling; comparing an attribute of the first near-field signal to an attribute of a second near-field signal received from a second substance.

In another example embodiment, further comprising: indicating that the first substance is same as the second substance if the attribute of the first substance is within a predetermined range of the attribute of the second substance.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Near-field electric and magnetic induction (NFEMI) devices utilize non-propagating quasi-static fields, whereas RF devices propagate an RF plane wave through free space.

The quasi-static characteristic of the near-fields is the result of antenna dimensions in combination with the carrier frequency. The majority of the energy is stored in the form of magnetic and electric fields and only a small amount of RF energy propagates in free space.

Small antenna geometries compared with the carrier wavelength are candidate for near field communication since they do not generate radiating waves in free space. Such an antenna can be a coil antenna that allows near field magnetic induction (NFMI). Other antennas communicate by means of both magnetic (H) and electric (E) near-fields via near field electric and magnetic induction.

To be discussed herein are example embodiments of NFEMI and NFMI devices which, using non-contact capacitive coupling to one or more substances (e.g. fluid, solid, gas), are used identify, differentiate, quality control, or perform other checks on the substance by means of the magnetic and electric near-fields.

For example, transmitter and receiver near-field devices, can be positioned at different locations along the substance and attributes of the received near-field signal can be used to either identify the substance or ensure that the substance falls within a quality control range as compared to reference attributes from a known reference substance.

Note that various embodiments of the near-field device may include: control circuitry, microprocessors, microcontrollers, digital signal processors, data processing units, human interface units, and antennas. Such antennas when in close proximity to the substance will generate fields that are substantially confined near the substance, thus providing a strong near-field signal for collecting and analyzing the substance's near-field attributes.

Such near-field attributes may include: a signal strength, a signal to noise ratio, a voltage, an attenuation, a conductivity, or another electrical parameter.

The near-field device to be discussed can be used in different possible applications, including: medical, pharmaceutical, industrial, manufacturing, production lines, assembly lines, food processing, mixing, diluting, calibration, and quality control applications.

Figure 1:
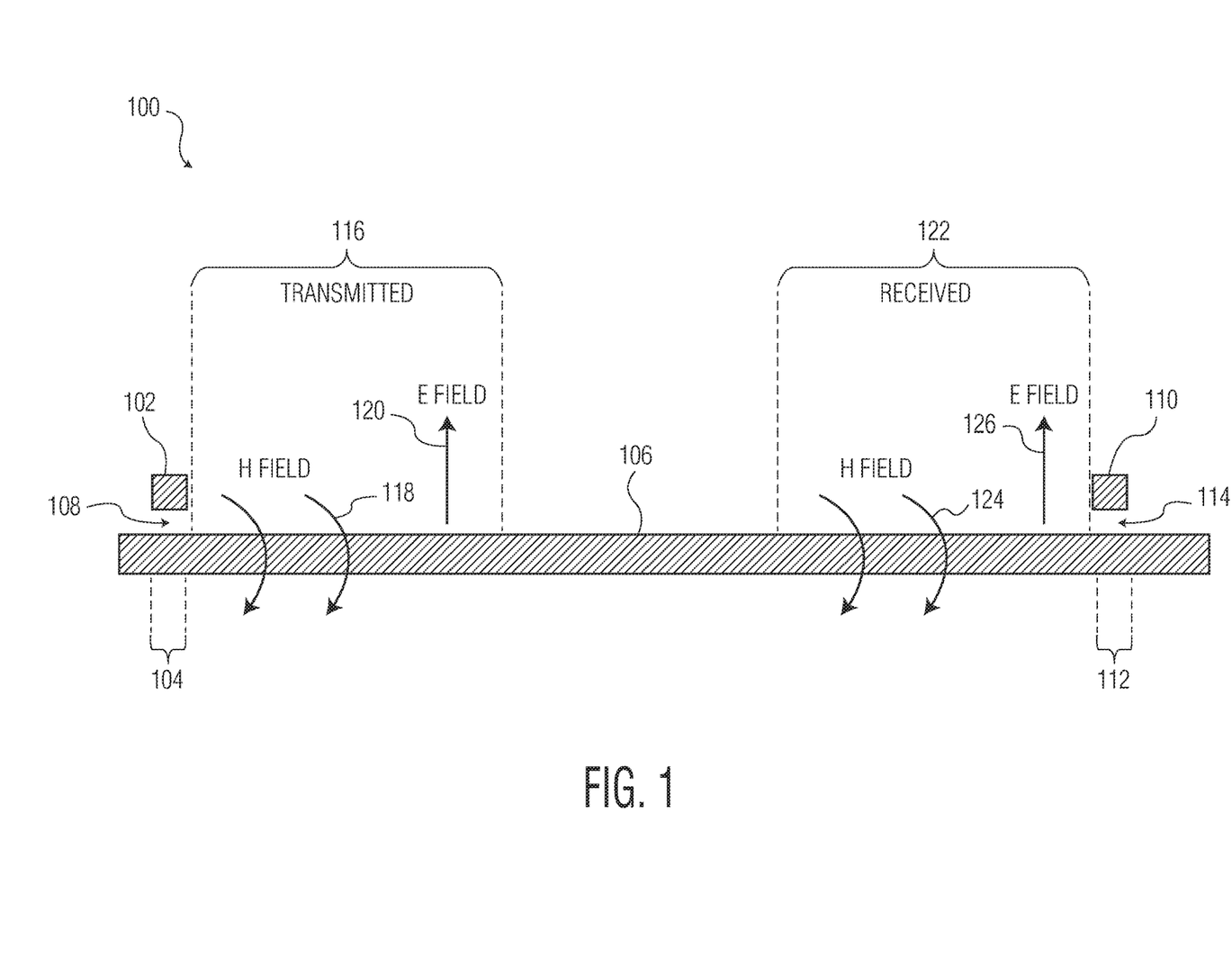
FIG. 1 is an example first application of a set of near-field devices.

FIG. 1 is an example first application 100 of a set of near-field devices 102, 110. The example first application 100 includes the first near-field device 102 (e.g. for near-field signal transmission and/or reception) positioned at a first location 104 along a substance 106. The first near-field device 102 includes a near-field transmitter antenna (not shown), a transmitter circuit (not shown), an encoder circuit (not shown) and is separated from the substance 106 by a dielectric 108 (e.g. air-gap for capacitive coupling).

This example first application 100 also includes a second near-field device 110 (e.g. for near-field signal reception and/or transmission) positioned at a second location 112 along the substance 106. The second near-field device 110 includes a near-field receiver antenna (not shown), a receiver circuit (not shown), a decoder circuit (not shown) and a dielectric 114 (e.g. another air-gap for capacitive coupling).

The substance 106 can be a liquid, solid, gas, plasma, saline, glucose, insulin, a structure, an assembly of parts, a mixture, a food, a set of items, etc. that includes at least one of: an atomic characteristic, a molecular characteristic, a cellular characteristic, a mixture characteristic, a structural characteristic, and a conductive characteristic. a quantity characteristic, or a volume characteristic.

The first near-field device 102 uses the encoder to generate a transmitted near-field signal 116 having an H-Field 118 (i.e. magnetic near-field) component and an E-Field 120 (i.e. electric near-field) component. The first near-field device 102 transmits the near-field signal 116 to the substance 106 through the transmitter's dielectric 108 (i.e. capacitive coupling).

The second near-field device 110 receives a near-field signal 122 from the substance 106 through the receiver's dielectric 114 (i.e. capacitive coupling). This received near-field signal 122 includes attributes that correspond to the transmitted near-field signal 116, but due to the first substance's 106 atomic, molecular, mixture, structural, conductive, quantity and/or volume characteristics, have an H-Field 124 (i.e. magnetic near-field) component and an E-Field 126 (i.e. electric near-field) component, which may or may not differ from the H-Field 118 and E-Field 120 components based on the substance's 106 attributes.

These attributes of the received near-field signal 122 may include at least one of: a signal strength, a signal to noise ratio, a voltage, an attenuation, a conductivity, or another electrical parameter.

Note that the H-field 118, 124 and E-field 120, 126 arrows in FIG. 1 illustrate the magnetic and electric near-field vectors along the substance 106. The near-field transmitter antenna is designed so that the magnetic field vector is curved around the substance 106. The electric field vector is perpendicular to the substance 106 when the substance 106 is conductive. The magnetic field and the electric field are distributed over the length of the substance 106. The antenna of the second near-field device 110 is able to convert the H-Field 124 and the E-Field 126 of the received near-field signal 122 into voltages that can be processed by the second near-field device 110.

In various example embodiments, the dielectrics 108, 114 for capacitive coupling can be either air-gaps, a container, or some other dielectric medium between the substance 106 and the outside of the near-field devices 102, 110. When the dielectrics 108, 114 are formed by a substantially non-conductive container, such container can hold a liquid, a gas, a mixture, or perhaps a set of items (e.g. perhaps for measuring a quantity or volume when filling containers with the substance 106).

The decoder circuit in the second near-field device 110 is configured to compare the attributes of the received near-field signal 122 from the substance 106 to attributes of another received near-field signal (not shown) from a second substance in an apparatus substantially similar to the example first application 100 shown in FIG. 1. The second substance in some example embodiments is a known substance that functions as a calibration substance or a standard.

In one example embodiment, the decoder circuit is configured to indicate the substance 106 is substantially same as the known second substance if the attributes of the substance 106 are within a predetermined range of the attributes of the second substance.

In another example embodiment, the decoder circuit is configured to indicate the substance 106 is different from the second substance if the attributes of the substance 106 are outside of a predetermined range of the attributes of the second substance.

Also, in another example embodiment, the decoder circuit is configured to assign a quality level to the substance 106 based on how close the attributes of the substance 106 are to the attributes of the second substance.

The near-field transmitter antenna can be separated from the near-field receiver antenna over a range of distances (e.g. perhaps 20 cm to 100 cm). The separation however can be increased by using larger transmit voltages to meters.

In NFMI and NFEMI embodiments, the near-field signal includes a carrier frequency that is in some examples ≤30 MHz. However higher frequencies are also possible.

The example first application 100 of a set of near-field devices 102, 110 can be used in a variety of applications, including: medical, pharmaceutical, industrial, manufacturing, production lines, assembly lines, food processing, mixing, diluting, calibration, and quality control applications.

Figure 2:
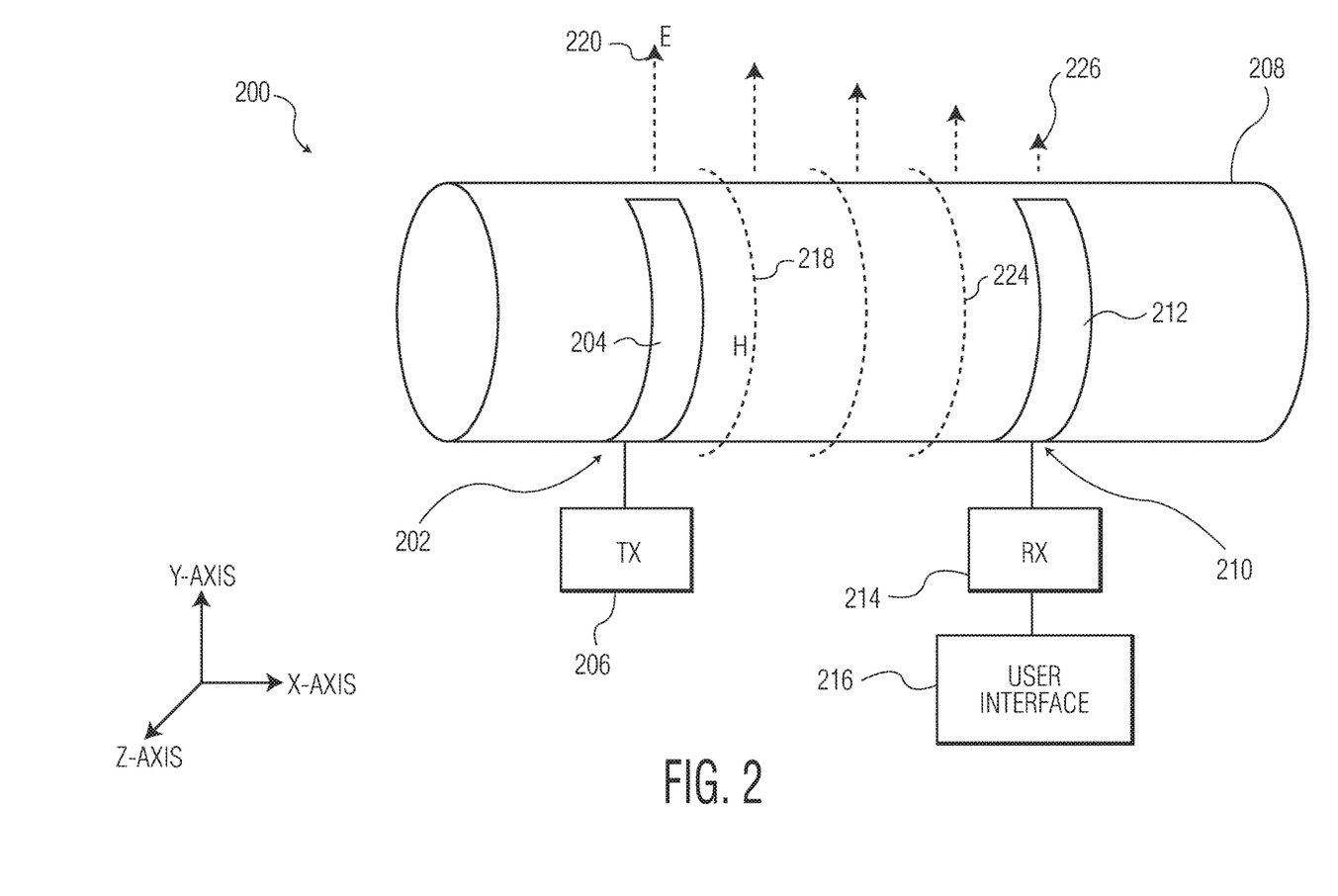
FIG. 2 is an example second application of the set of near-field devices.

FIG. 2 is an example second application 200 of the set of near-field devices. The example second application 200 of a set of near-field devices includes: a near-field transmitter and a near-field receiver.

The near-field transmitter is positioned at a first location 202 along a container 208. The near-field transmitter includes a near-field transmitter antenna 204 and a transmitter and encoder circuit 206. The near-field transmitter generates a transmitted near-field signal having an H-Field 218 (i.e. magnetic near-field component) and an E-Field 220 (i.e. electric near-field component).

The near-field receiver is positioned at a second location 210 along the container 208. The near-field receiver includes a near-field receiver antenna 212, a receiver and decoder circuit 214, and a user interface 216. The near-field receiver receives a received near-field signal having an H-Field 224 (i.e. magnetic near-field component) and an E-Field 226 (i.e. electric near-field component).

The container 208 is configured to hold a substance to be measured. In some example embodiments the container 208 is a non-conductive dielectric so as to enable capacitive coupling between the substance and the antennas 204, 212. The container 208 material can include: polymers, glass, or organics. In one example, the near-field antennas 204, 212 also function as mechanical clamps for holding and securing the container 208. In one example embodiment, a distance between the antenna 204, 212 locations 202, 210 is 10 to 20 cm; however, in other examples the distance can be greater or lesser.

The transmitter and encoder circuit 206 generates a voltage and a current at a frequency that is converted by the near-field transmitter antenna 204 into the H-Field 218 and E-Field 220 of the transmitted near-field signal. The frequency that can be used is defined by dimensions of the antennas 204, 212. The wavelength of the transmitted near-field signal should be much larger than sizes of the antennas 204, 212 to ensure that only near-field is generated. For example, if the radio frequency is 10 MHz, antenna 204, 212 sizes can be several centimeters.

Since the substance (e.g. a fluid) in the container 208 is conductive, the E-Field vector 220 will be orthogonal to the container 208. The H-Field vector 218 that is encircling the container 208 can also be used. Both fields 220, 218 follow the container's 208 shape and are attenuated in amplitude along a length of the container 208 by the substance.

At the second location 210 of the near-field receiver antenna 212, the received near-field signal (i.e. the H-Field 224 and the E-Field 226) are attenuated and are converted by the receiver and decoder circuit 214 to voltages and currents. The amount of measured attenuation is then related to an attribute (e.g. an electrical conductivity) of the substance under test.

Figure 3:
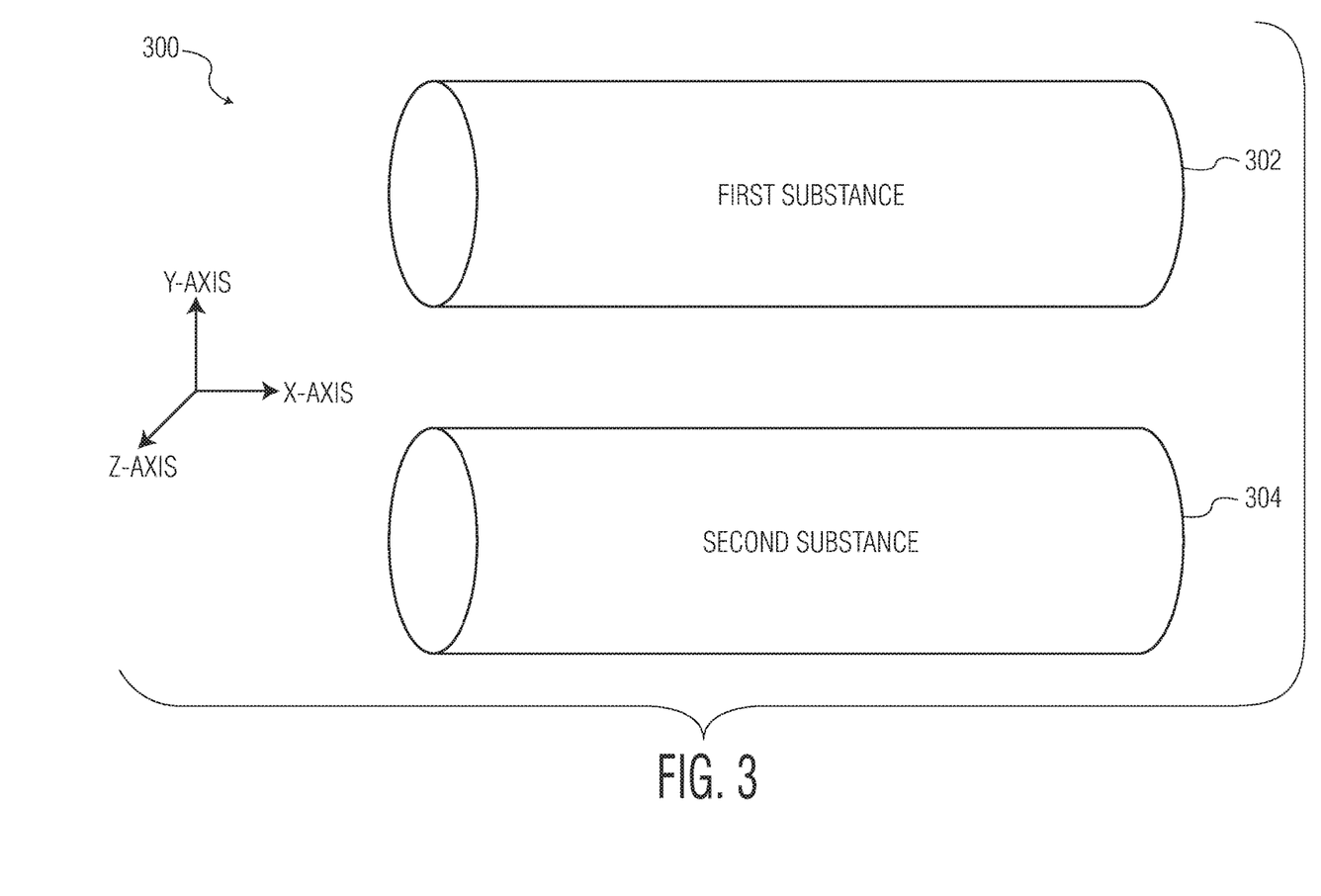
FIG. 3 is an example of a first substance and a second substance.

FIG. 3 is an example 300 of a first substance 302 and a second substance 304. In some example embodiments, the substances 302, 304 are solids measured using the example first application 100 of FIG. 1. In other example embodiments, the substances 302, 304 are liquids inside containers such as the container 208 of FIG. 2 and are measured using the example second application 200, and are placed on, clipped into or otherwise held by the antennas 204, 212.

In some example embodiments, just a received near-field signal attribute difference between the substances 302, 304 needs to be known. In other example embodiments, the second substance 304 is known and functions as a reference for identifying, distinguishing or measuring a quality level of the first substance 302.

Such a known second substance 304 reference can in one example be calibrated and implemented as follows. A reference fluid (e.g. the second substance 304) having a known electric conductance is inserted into the container 208 of the second application 200 system. The near-field transmitter antenna 204 starts generating the near-fields. The receiver and decoder circuit 214 measures a received signal strength attribute, and the electric conductance of the reference fluid is calibrated. Additional known substances can also be measured in this way and stored in a memory inside the user interface 216. An extended database can thus be built with many reference fluids based on temperature or other environment parameters.

Next a fluid under test (e.g. the first substance 302) is inserted in the container 208 of the second application 200 system. The near-field transmitter antenna 204 again starts generating the near-fields. The receiver and decoder circuit 214 then measure a test signal strength, this is the test fluid signal strength. From the database inside the user interface 216, the fluid under test can be identified.

Figure 4:
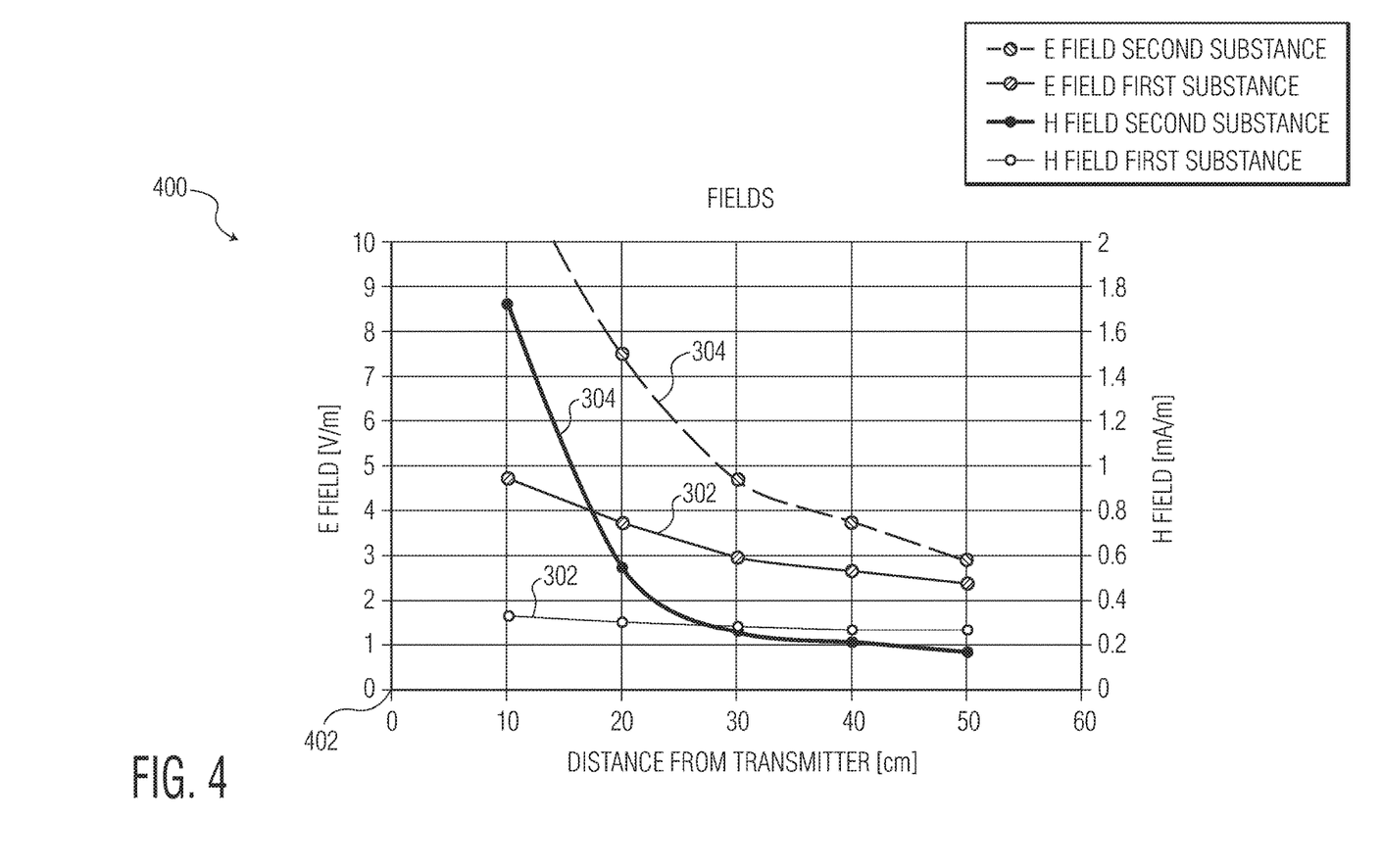
FIG. 4 are example near-field signals received over various distances from the first substance and the second substance.

FIG. 4 are example 400 near-field signals received over various distances from the first substance 302 and the second substance 304. Either the example first application 100 set up of FIG. 1 or the example second application 200 of FIG. 2 could be used to generate the example 400 field-strength signal data.

In this example 400 location 402 corresponds to either first location 104 or first location 202. The rest of the data points in this example 400 correspond to either the second location 112 or the second location 210 at various distances from location 402. While H and E field-strength are an example attributes being measured for the first and second substances 302, 304, similar data points could be collected in other example embodiments corresponding to other attributes of the first and second substances 302, 304.

Figure 5:
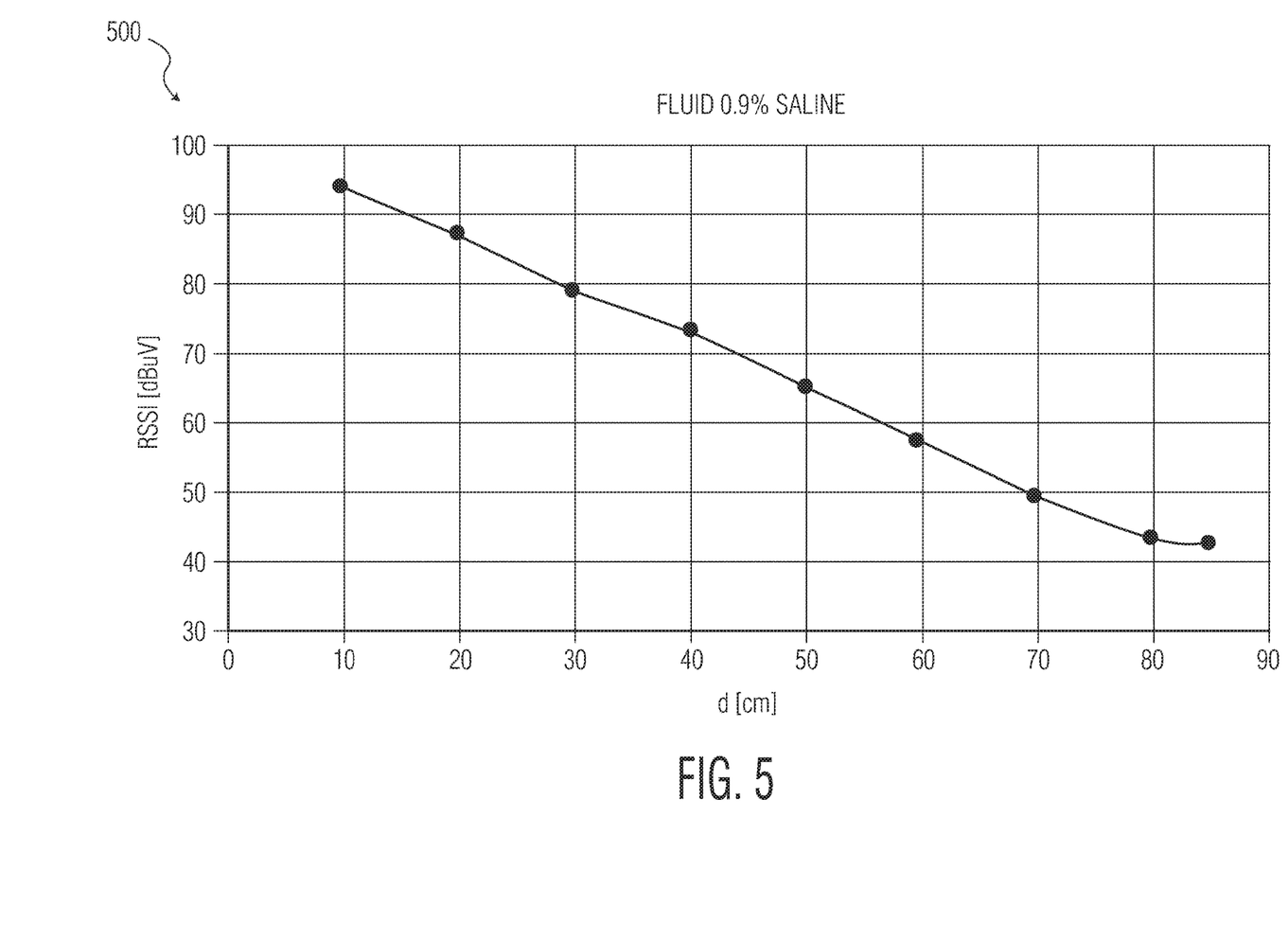
FIG. 5 shows an example received near-field signal, over various distances, from a saline solution substance.

FIG. 5 shows an example received near-field signal, over various distances, from a saline solution substance. Since saline is a liquid, the example second application 200 of FIG. 2 could be used to generate this example 500 received signal strength indicator (RSSI) (e.g. voltage) data. Here the example 500 RSSI corresponds to a 0.9% Saline solution RSSI received near-field signal at various distances from a transmitted near-field signal.

The example 500 graph shows attenuation of the RSSI as a function of distance between the near-field transmitter antenna 204 and near-field receiver antenna 212. For example, when the example second application 200 system of FIG. 2 has a 20 cm separation between the antennas 204, 212, then the RSSI is about 87 dbuV, which is a relatively strong signal.

Figure 6:
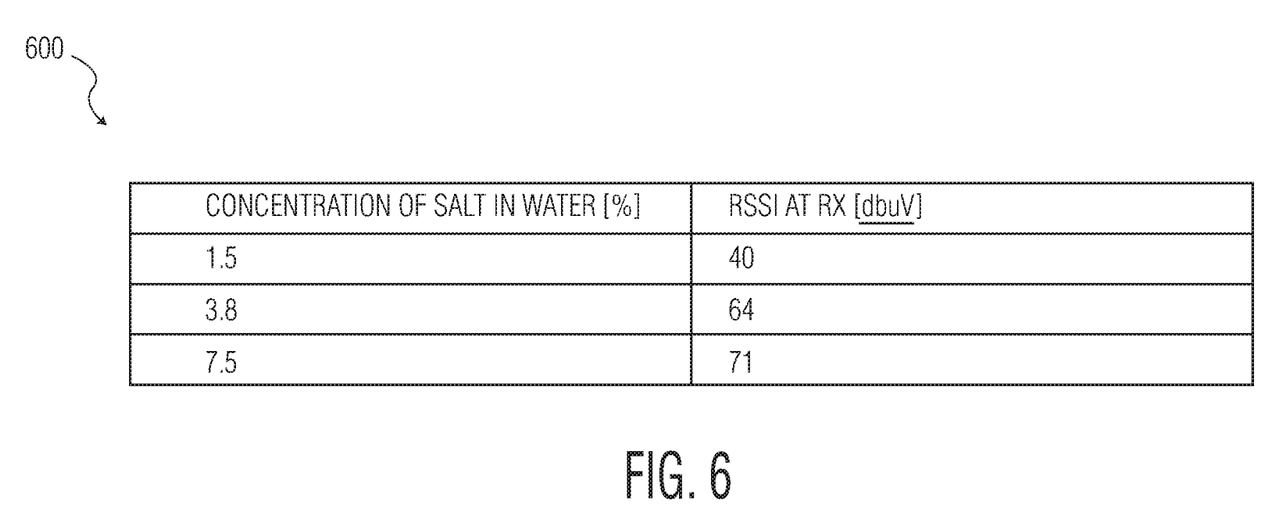
FIG. 6 are example received near-field signals, at a same fixed distance, from various saline solutions.

FIG. 6 are example 600 received near-field signals, at a same fixed distance, from various saline solutions. In this example 600 data set the container 208 is a plastic pipe about 5 mm in diameter and 1 meter long. The RSSI corresponds to received voltages at the near-field receiver for different concentrations of salt water. Here, the RSSI depends on the salt concentration which directly influences the measured electric conductivity.

Various instructions and/or operational steps discussed in the above Figures can be executed in any order, unless a specific order is explicitly stated. Also, those skilled in the art will recognize that while some example sets of instructions/steps have been discussed, the material in this specification can be combined in a variety of ways to yield other examples as well, and are to be understood within a context provided by this detailed description.

In some example embodiments these instructions/steps are implemented as functional and software instructions. In other embodiments, the instructions can be implemented either using logic gates, application specific chips, firmware, as well as other hardware forms.

When the instructions are embodied as a set of executable instructions in a non-transient computer-readable or computer-usable media which are effected on a computer or machine programmed with and controlled by said executable instructions. Said instructions are loaded for execution on a processor (such as one or more CPUs). Said processor includes microprocessors, microcontrollers, processor modules or subsystems (including one or more microprocessors or microcontrollers), or other control or computing devices. A processor can refer to a single component or to plural components. Said computer-readable or computer-usable storage medium or media is (are) considered to be part of an article (or article of manufacture). An article or article of manufacture can refer to any manufactured single component or multiple components. The non-transient machine or computer-usable media or mediums as defined herein excludes signals, but such media or mediums may be capable of receiving and processing information from signals and/or other transient mediums.

It will be readily understood that the components of the embodiments as generally described herein and illustrated in the appended figures could be arranged and designed in a wide variety of different configurations. Thus, the detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

What is claimed is:

1. A near-field device, comprising:
   a near-field receiver coupled to a near-field receiver antenna and a decoder circuit, wherein the near-field receiver antenna is configured to be capacitively coupled at a first location of a first substance within a container, to receive both a first non-propagating quasi-static magnetic near-field signal and a first non-propagating quasi-static electric near-field signal from the first substance through the receiver's capacitive coupling, wherein the non-propagating quasi-static magnetic near-field signal has a magnetic field vector curved around the container and the non-propagating quasi-static electric near-field signal has an electric field vector perpendicular to the container, and compare an attribute of the first non-propagating quasi-static magnetic and electric near-field signals to an attribute of second non-propagating quasi-static magnetic and electric near-field signals received from a second substance, wherein the second substance is a known substance that functions as a calibration substance or a standard.

2. The near-field device of claim 1, wherein the decoder circuit is configured to indicate the first substance is same as the second substance after the attribute of the first substance is within a predetermined range of the attribute of the second substance.

3. The near-field device of claim 1, wherein the decoder circuit is configured to indicate the first substance is different from the second substance after the attribute of the first substance is outside of a predetermined range of the attribute of the second substance.

4. The near-field device of claim 1, wherein the decoder circuit is configured to assign a quality level to the first substance based on how close the attribute of the first substance is to the attribute of the second substance.

5. The device of claim 1: wherein the first substance includes at least one of: liquid, solid, gas, plasma, saline, glucose, insulin, a structure, an assembly of parts, a mixture, a food, or a set of items.

6. The device of claim 1: wherein the attribute of the received near-field signal is at least one of: a signal strength, a signal to noise ratio, a voltage, an attenuation, a conductivity, or another electrical parameter.

7. The device of claim 1: wherein the attribute of the first near-field signal is affected by at least one of the first substance characteristics: an atomic characteristic, a molecular characteristic, a cellular characteristic, a mixture characteristic, a structural characteristic, a conductive characteristic, a quantity characteristic, or a volume characteristic.

8. The device of claim 1: wherein the capacitive coupling between the receiver antenna and the first substance includes at least one of: an air gap or a container.

9. The device of claim 1: further comprising a container configured to hold the first substance.

10. The device of claim 9: wherein the first substance is more conductive than the container.

11. The device of claim 9: wherein the near-field receiver antenna substantially conforms to a shape of the container.

12. The near-field device of claim 1: wherein the first near-field signal includes a carrier frequency that is 30 MHz.

13. The near-field device of claim 1, further comprising:
another near-field device including a near-field transmitter coupled to a near-field transmitter antenna and an encoder circuit, wherein the near-field transmitter antenna is configured to be capacitively coupled at a second location on the first substance, the encoder circuit is configured to generate the first non-propagating quasi-static magnetic and electric near-field signals and the near-field transmitter antenna is configured to transmit the first non-propagating quasi-static magnetic and electric near-field signals to the first substance through the transmitter's capacitive coupling.

14. The near-field device of claim 13, wherein the near-field receiver and transmitter antennas are configured to physically hold the first substance within the container.

15. The near-field device of claim 14, wherein the receiver and transmitter antennas are configured to permit the first substance to be removed and replaced with additional substances.

16. The near-field device of claim 13, wherein the first non-propagating quasi-static electric near-field signal is generated by an electric near-field antenna in the transmitter antenna and received by a magnetic near-field antenna in the receiver antenna.

17. The near-field device of claim 13, wherein the first non-propagating quasi-static magnetic near-field signal is generated by a magnetic near-field antenna in the transmitter antenna and received by an electric near-field antenna in the receiver antenna.

18. The near-field device of claim 1, wherein the non-propagating quasi-static magnetic near-field signal has a magnetic field vector curved around the container and the non-propagating quasi-static electric near-field signal has an electric field vector perpendicular to the container.

19. A method of processing a near-field signal, comprising:
receiving both a first non-propagating quasi-static magnetic near-field signal and a first non-propagating quasi-static electric near-field signal from a first substance within a container, through a capacitive coupling;
comparing an attribute of the first non-propagating quasi-static magnetic and electric near-field signal to an attribute of second non-propagating quasi-static magnetic and electric near-field signal received from a second substance, wherein the non-propagating quasi-static magnetic near-field signal has a magnetic field vector curved around the container and the non-propagating quasi-static electric near-field signal has an electric field vector perpendicular to the container, and the second substance is a known substance that functions as a calibration substance or a standard.

20. The method of claim 19, further comprising:
indicating that the first substance is same as the second substance after the attribute of the first substance is within a predetermined range of the attribute of the second substance.

* * * * *